United States Patent [19]

Leuchtenberger et al.

[11] Patent Number: 4,609,623

[45] Date of Patent: Sep. 2, 1986

[54] MICROBIOLOGICALLY PRODUCED D-2-HYDROXY-4-METHYLPENTANOIC ACID DEHYDROGENASE, PROCESS FOR ITS PRODUCTION AND ITS USE

[75] Inventors: Wolfgang Leuchtenberger, Bruchkobel; Werner Hümmel, Titz; Maria-Regina Kula, Wolfenbüttel; Horst Schütte, Salzgitter, all of Fed. Rep. of Germany

[73] Assignees: Degussa AG, Frankfurt; Society for Biotechnical Research, Braunschweig-Stockheim, both of Fed. Rep. of Germany

[21] Appl. No.: 617,738

[22] Filed: Jun. 6, 1984

[30] Foreign Application Priority Data

Jun. 7, 1983 [DE] Fed. Rep. of Germany ....... 3320495

[51] Int. Cl.$^4$ .......................... C12P 11/00; C12P 7/40; C12P 7/42; C12N 9/02; C12N 9/04; C12R 1/225; C12R 1/245; C12R 1/01
[52] U.S. Cl. ..................................... 435/130; 435/136; 435/146; 435/189; 435/190; 435/853; 435/856; 435/822

[58] Field of Search ............... 435/130, 136, 146, 190, 435/189

[56] References Cited

U.S. PATENT DOCUMENTS 4,326,031  4/1982  Wandrey et al. .................. 435/146
4,530,903  7/1985  Leuchtenberger et al. ........ 435/130

Primary Examiner—Lionel M. Shapiro
Attorney, Agent, or Firm—Cooper, Dunham, Griffin & Moran

[57] ABSTRACT

The enzyme D-2-hydroxy-4-methylpentanoic acid dehydrogenase has been prepared by culturing readily available Lactobacillus or Leuconostoc, microorganisms, such as *Lactobacillus casei ssp. pseudoplantarum* and *Leuconostoc mesenteroides*. The microbiologically produced enzyme has special characteristics and is capable of converting D-2-hydroxycarboxylic acids, such as D-2-hydroxy-4-methylpentanoic acid to the corresponding 2-ketocarboxylic acid and is capable of enzymatically converting 2-ketocarboxylic acids, such as 2-keto-4-methylpentanoic acid and 2-ketobutyric acid to the corresponding D-2-hydroxycarboxylic acid.

15 Claims, 2 Drawing Figures

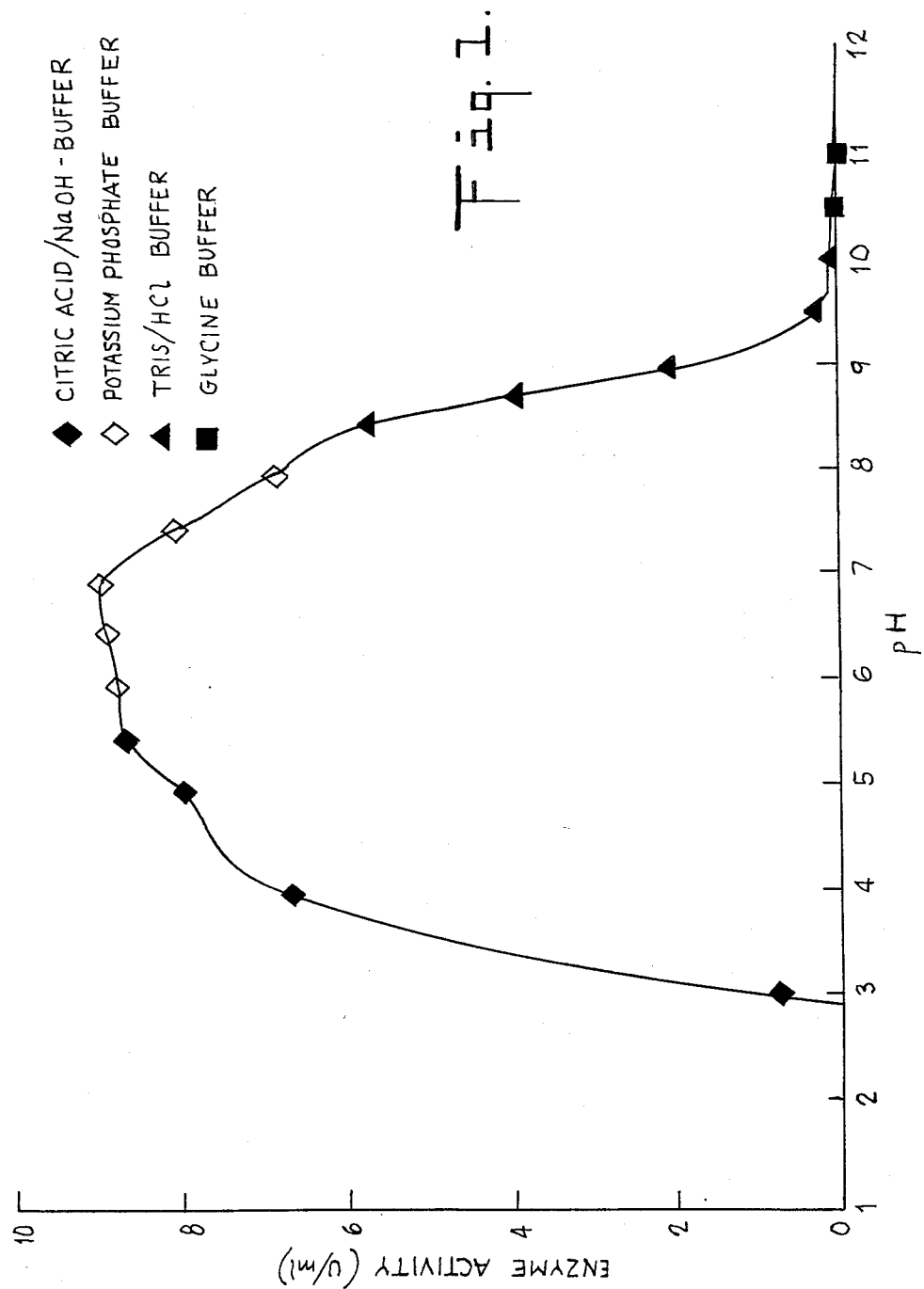

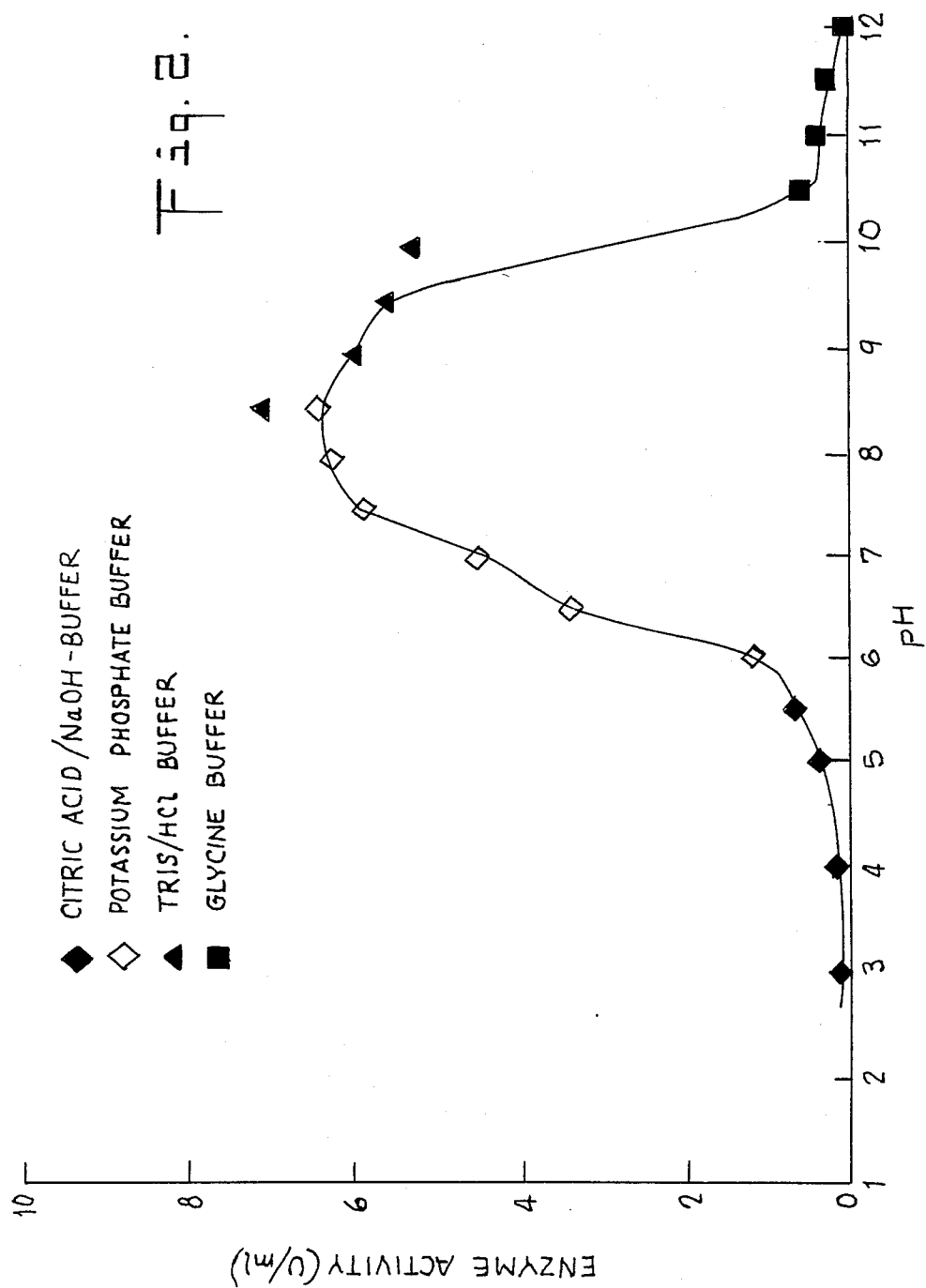

MICROBIOLOGICALLY PRODUCED D-2-HYDROXY-4-METHYLPENTANOIC ACID DEHYDROGENASE, PROCESS FOR ITS PRODUCTION AND ITS USE

BACKGROUND OF THE INVENTION

This invention relates to the production of a special enzyme. More particularly, this invention relates to the production of a special enzyme employing a microorganism which is cultured to produce the enzyme and the recovery of the resulting produced enzyme from the cultured microorganism.

It is an object of this invention to employ a readily available microorganism for the production of the desired enzyme.

It is another object of this invention to microbiologically produce the enzyme by culturing these readily available microorganisms and then recovering the enzyme from the resulting cultured microorganisms.

How these and other objects of this invention are achieved will become apparent in the light of the accompanying disclosure made with reference to the drawings wherein:

FIG. 1 graphically illustrates the reaction velocity expressed as enzyme activity in U/ml as a function of pH; and wherein FIG. 2 also graphically illustrates the reaction velocity expressed as enzyme activity in U/ml of the dehydrogenation reaction.

SUMMARY OF THE INVENTION

The enzyme D-2-hydroxy-4-methylpentanoic acid-dehydrogenase has been prepared. This enzyme has been microbiologically prepared by culturing a readily available microorganism of the genus Lactobacillus or the genus Leuconostoc. Upon culturing the microorganism, the resulting microbiologically produced enzyme is recovered from the cultured microorganism. The resulting recovered microbiologically prepared D-2-hydroxy-4-methylpentanoic acid-dehydrogenase is characterized by the following properties:

(a) catalyzes, with the coenzyme nicotinamide-adeninedinucleotide (NAD+), the dehydrogenation of D-2-hydroxy-4-methylpentanoic acid to 2-keto-4-methylpentanoic acid, (b) catalyzes, with the coenzyme NAD+, the dehydrogenation of additional D-2-hydroxycarboxylic acids to the corresponding 2-ketocarboxylic acids and in addition shows special activity with respect to D-2-hydroxypentanoic acid, D-2-hydroxyhexanoic acid, D-2-hydroxyoctanoic acid, D-2-hydroxy-4-(methylmercapto)butyric acid and D-2-hydroxy-3-phenylpropionic acid, (c) catalyzes the stereoselective reduction of 2-keto-4-methylpentanoic acid to D-2-hydroxy-4-methylpentanoic acid with NADH as coenzyme, (d) catalyzes the stereoselective reduction of additional 2-ketocarboxylic acids, especially of 2-ketobutyric acid, 2-ketopentanoic acid, 2-keto-3-methylbutyric acid, 2-ketohexanoic acid, 2-keto-3-methylpentanoic acid, 2-ketooctanoic acid, 2-keto-3-mercaptopropionic acid, 2-keto-4-(methylmercapto)-butyric acid and 2-keto-3-phenylpropionic acid to the corresponding D-2-hydroxycarboxylic acids with NADH as coenzyme.

(e) an optimal pH-range of 7.5 to 9.0 for the dehydrogenation reaction, (f) an optimal pH-range of 5.5 to 7.0 for the reduction reaction, and (g) a pH-stability range of 3.5 to 10.

The special enzyme of this invention D-2-hydroxy-4-methylpentanoic acid dehydrogenase is useful for the enzymatic conversion of D-2-hydroxy-4-methylpentanoic acid, D-2-hydroxypentanoic acid, D-2-hydroxyhexanoic acid, D-2-hydroxyoctanoic acid, D-2-hydroxy-4-(methylmercapto)-butyric acid and D-2-hydroxy-3-phenylpropionic acid to the corresponding 2-ketocarboxylic acid. Also, the special enzyme of this invention enzymatically converts 2-keto-4-methylpentanoic acid, 2-ketobutyric acid, 2-ketopentanoic acid, 2-keto-3-methylbutyric acid, 2-ketohexanoic acid, 2-keto-3-methylpentanoic acid, 2-ketooctanoic acid, 2-keto-3-mercaptopropionic acid, 2-keto-4-(methylmercapto)-butyric acid, and 2-keto-phenylpropionic acid to the corresponding D-2-hydroxycarboxylic acid.

The enzyme of this invention is produced by culturing the readily available Lactobacillus and Leuconostoc microorganisms employing an aqueous nutrient or culture medium, such as a nutrient or culture medium which contains a source of carbon, nitrogen, vitamins, growth substances, if necessary or desirable, and mineral salts. Usually the culture medium has a pH of about 6.5 at the start of the growth or culturing period. The resulting cultured cells are recovered or removed or harvested by suitable means, such as centrifugation, at about the end of the culturing operation and then disintegrated in a suspension and buffered at about pH 7 and the resulting microbiologically produced enzyme recovered or isolated from the extract.

DETAILED DESCRIPTION OF THE INVENTION

The microorganisms of the genus Lactobacillus or the genus Leuconostoc are advantageously employed in the practices of this invention for the production of the enzyme D-2-hydroxy-4-methylpentanoic acid dehydrogenase, especially so since these microorganisms are generally available. A suitable source for these microorganisms is the German Microorganism Collection (DSM) located at Goettingen, Federal Republic of Germany. The microorganisms employed in the practices of this invention are identified not only by the conventional names of the microorganisms but also by their DSM accession number.

Suitable readily available microorganisms employed in the practices of this invention for the production of the enzyme D-2-hydroxy-4-methylpentanoic acid dehydrogenase include *Lactobacillus casei ssp. pseudoplantarum* (DSM 2008) *Lactobacillus casei ssp. alactosus* (DSM 20020), *Lactobacillus casei ssp. rhamnosus* (DSM 20178), *Leuconostoc oenos* (DSM 20252), *Lueconostoc lactis* (DSM 20202) and *Leuconostoc mesenteroides* (DSM 20343).

Microorganisms of the genus Lactobacillus and the genus Leuconostoc are well known, see particularly Bergey's *Manual of Determinative Bacteriology*, 7th Ed. (1957), The Williams & Wilkins Co., Baltimore, Md., U.S.A., pages 531, 532 and pages 542–552. The disclosures of this publication are herein incorporated and made part of this disclosure.

Microorganisms of the genus Leuconostoc disclosed therein include *Leuconostoc mesenteroides, Leuconostoc dextranicum, Leuconostoc citrovorum* and microorganisms of the genus Lactobacillus disclosed therein include *Lactobacillus caucasicus, Lactobacilus lactis, Lactobacillus helveticus, Lactobacillus acidophilus, Lactobacillus bifudus, Lactobacillus bulgaricus, Lactobacillus thermophilus, Lactobacillus delbrueckii, Lactobacillus casei, Lactobacillus leichmannii, Lactobacillus plantarum, Lactobacillus pastorianus, Lactobacillus buchneri, Lactobacillus brevis* and *Lactobacillus fermenti.*

The enzyme D-lactate-dehydrogenase (E.C.1.1..28) is known to effect the stereospecific reduction of 2-ketocarboxylic acid to D-2-hydroxycarboxylic acids. The enzyme of this invention D-2-hydroxy-4-methylpentanoic acid dehydrogenase, however, is different from the D-lactate dehydrogenase enzyme since D-2-hydroxy-4-methylpentanoic acid dehydrogenase does not accept pyruvate as a substrate. Also, the enzyme D-2-hydroxy-fatty acid dehydrogenase (E.C.1.1.1.98) has been isolated from rat kidneys where it participates in the β-oxidation of long chain fatty acid with respect to this enzyme, only 2-hydroxystearate has been described as a substrate.

The new enzyme of this invention D-2-hydroxy-4-methylpentanoic acid dehydrogenase was determined by photometric testing. The test volume (3.00 ml) contained in 0.1M phosphate buffer at pH 7.0, 0.235 mM NADH, 0.79 mM 2-keto-4-methylpentanoic acid and limiting quantities of enzyme. The decrease of the NADH-extinction at 340 nm and 30° C. was measured; a blank value obtained when the test volume was incubated without the 2-ketocarboxylic acid was subtracted. The enzyme activity is expressed in international units (U), in which 1U catalyzes the consumption of $10^{-6}$ Mol NADH.min$^{-1}$.ml$^{-1}$. For the calculation, a molar extinction coefficient for NADH at 340 nm of $6.22.10^3$ was used. With the test condition described, D-2-hydroxy-4-methylpentanoic acid dehydrogenases as well as L-2-hydroxy-4-methylpentanoic acid dehydrogenases was detected. Positive strains were again tested with chiral, commercially unavailable D-2-hydroxy-4-methylpentanoic acid as substrate. Only the D-2-hydroxy-4-methylpentanoic acid dehydrogenase of the invention showed activity to D-2-hydrocarboxylic acids, while the L-2-hydroxy-4-methylpentanoic acid dehydrogenase is inactive. A further proof of the stereospecificity of the catalytic conversion was obtained by experiments in a membrane reactor, which will be described later in detail.

The measured specific activities and volume activities of the individual D-2-hydroxy-4-methylpentanoic acid dehydrogenase-producing microorganisms in the crude extract are shown in Table 1. Activity measurements with two additional 2-ketocarboxylic acids as substrate showed that the enzyme from *Lactobacillus casei ssp. pseudoplantarum* (DSM 20008) has the broadest substrate spectrum, and is therefore especially suited to convert a number of D-2-hydrocarboxylic acids with good activity. (See Table 1).

TABLE 1

Enzyme activity in the raw extract of various microorganisms

| Strain | DSM Number | Enzyme activities with Substrate | | | | | |
|---|---|---|---|---|---|---|---|
| | | 1 | | 2 | | 3 | |
| | | U/mg | U/l | U/mg | U/l | U/mg | U/l |
| *Leuconostoc oenos* | 20 252 | 18.13 | 700 | 1.35 | 52 | 1.77 | 69 |
| *Leuconostoc mesenteroides* | 20 343 | 1.67 | 101 | 2.86 | 173 | 9.30 | 563 |
| *Leuconostoc lactis* | 20 202 | 1.03 | 53 | 0.45 | 23 | 0 | 0 |
| *Lactobacillus casei ssp. pseudoplantarum* | 20 008 | 0.58 | 108 | 1.88 | 316 | 7.25 | 1216 |
| *Lactobacillus casei ssp. rhamnosus* | 20 178 | 0.38 | 43 | 1.15 | 128 | 5.93 | 660 |
| *Lactobacillus casei ssp. alactosus* | 20 020 | 0.49 | 42 | 0.94 | 180 | 3.11 | 594 |

Substrate:
1 = 2-keto-4-methylpentanoic acid
2 = 2-keto-4-(methylmercapto)-butyric acid
3 = 2-keto-3-phenylpropionic acid
The specific enzyme activities (U/mg protein) and volume activities (U/l medium) are shown In the following, the production of the new enzyme from *Lactobacillus casei ssp. pseudoplantarum* (DSM 20008) is described by way of example:

1. Cultivation of the microorganism

For cultivation, *Lactobacillus casei ssp. pseudoplantarum* (DSM 20008) was grown in the following medium:

Glucose—20 g
Yeast extract—10 g
Meat extract—0.5 g
Sodium acetate—5 g
K$_2$HPO$_4$—2 g
MgSO$_4$—0.2 g
MnSO$_4$—0.05 g
De-ionized water—to 1 L.

The pH of this solution was adjusted to 6.5, and it was then sterilized for 15 minutes at 121° C. (2 bar). For cultivation, 5 ml of the medium was inoculated with a loop full of *Lactobacillus casei ssp. pseudoplantarum* from a punctural culture of an agar-tube, and incubated at 30° C. for 16 to 20 hours. 4 ml of the culture grown was then used as inoculant culture for 200 ml medium (in 500 ml Erlenmeyer flasks). After 20 to 24 hours, this 200 ml can be used as a pre-culture for a 10 L fermenter; thus, 200 L and 5,000 L could be inoculated. The pH, which drops in the course of the cultivation, was maintained at 5.0 with concentrated ammonia. The cultivation in the fermenter proceeded with mild agitation and gassing with nitrogen. Toward the end of the logarithmic growth phase, the culture was cooled and the cells harvested by centrifugation. In this way, 45 kg of centrifuged cell mass was obtained from 4,500 L of culture. The biomass can be stored for several months at −20° C. without major loss of activity.

2. Isolation and purification of the enzyme (a) Crude extract 500 g *Lactobacillus casei ssp. pseudoplantarum* (DSM 20008) wet mass was suspended in 50 mM phosphate buffer for pH 7.0 containing 0.1% (v/v) 2-mercaptoethanol. The final volume of 1,250 ml corresponds to a 40% cell suspension. The cells were treated either in a continuously operating glass-bead mill or a high pressure homogenizer. For this, the Dyno-Mill Type KDL manufactured by the Bachofen Company was used as a glass bead mill.

The mill containing 600 ml was filled with 0.25 to 0.5 mm glass beads, so that a bead load volume of 510 ml resulted (85%). The disintegration was carried out at a rotational speed of the agitator of 3,000 rpm and a flow rate of 5 L/h. The cooling jacket of the grinding mill as well as the tube shaft bearing were cooled with ethylene glycol solution at −20° C. during the operation, in order largely to eliminate heating of the product. After three passes, a degree of disintegration of >90% is attained. The pH of the suspension drops to 6.1 during homogenization, and is brought back to pH 7.0 with potassium hydroxide. As a high pressure homogenizer, the Manton Gaulin Type 15 M-8TA apparatus (A.P.V. Schröder GmbH, Lübeck), for example, may be employed. The cell suspension is disintegrated at 550 bars using a special valve designed for the disintegration of microorganisms, at a throughput rate of 54 L/hr. After two passes, a degree of disintegration rate of >90% is achieved. After each pass, the homogenate is cooled to a temperature below +10° C. by means of a heat exchange, in order to prevent heating of the product above 20° C. The pH of the suspension is adjusted to 7.0 after the disintegration.

(b) Liquid-liquid partition

The cell fragments should be separated from the crude extract according to DE-PS 26 39 129 with the first extraction step. For this purpose, an aqueous two-phase system is prepared, containing 20% (w/v) polyethylene glycol 1500, 8% (w/w) pH 7.0 phosphate buffer, and 1,250 ml crude extract in a 2.5-kg system. In order to reach equilibrium of partition, the two-phase system is stirred for one hour, and finally separated by centrifugation. Larger volumes are preferably separated continuously with a disc stack separator, for example Type Gyrotester B of α-Laval or Westfalia Type SAOH-205. The upper phase (1,440 ml) contains practically the entire activity (Yield 99%) of D-2-hydroxy-4-methyl-pentanoic acid dehydrogenase. The lower phase contains cell fragments and is discarded. The enzyme-containing upper phase is treated with 2% (w/v) polyethylene glycol 10,000, 8% (w/w) phosphate buffer for pH 6.0, and 0.4M sodium chloride, calculated on a final volume of 2,880 ml, and agitated for one hour. The polyethylene glycol-salt system formed is placed in a standing cylindrical vessel; the separation of phases is complete after several hours. In this partition step, the D-2-hydroxy-4-methylpentanoic acid dehydrogenase is extracted in the salt-containing lower phase. The separation of the phases proceeds by running off the lower phase.

(c) Diafiltration

The lower phase is concentrated with an Amicon hollow fiber module (Type H1P10), and diafiltered to a salt concentration of 50 mM with addition of pH 7.0 phosphate buffer.

(d) DEAE-Cellulose-Chromatography

The concentrated and diafiltered enzyme is pumped to a 5×30 cm column packed with Whatman-Cellulose DE 52. The DEAE-Cellulose was equilibrated against a buffer which contains 50 mM phosphate buffer of pH 7.0 and 0.1% (v/v) 2-mercaptoethanol. The column is then washed with about 2 L of starting buffer, and the enzyme finally eluted with a linear gradient (2×2 L) of 0 to 0.25M sodium chloride in starting buffer. The D-2-hydroxy-4-methylpentanoic acid dehydrogenase elutes with app. 0.1M sodium chloride. The active fractions are concentrated by ultrafiltration and stored at 4° C. The purification steps are summarized in Table 2.

TABLE 2

| Purification of D-2-hydroxy-4-methylpentanoic acid dehydrogenase | | | | | | |
|---|---|---|---|---|---|---|
| Purification Step | Volume ml | Protein mg | Total activity U | Spec. activity U/mg | Yield % | Enrichment-times |
| Crude extract | 1,250 | 30,500 | 18,625 | 0.61 | 100 | 1 |
| Upper phase I | 1,440 | 6,120 | 18,438 | 3.01 | 99 | 4.9 |
| Lower phase II | 1,060 | 3,795 | 15,857 | 4.18 | 85 | 6.9 |
| Diafiltration | 187 | 3,150 | 15,064 | 4.78 | 81 | 7.8 |
| DEAE-Cellulose | 493 | 424 | 10,545 | 24.87 | 57 | 40.8 |

The enzyme preparation obtained after the last stage can be used for technical purposes. By further chromatographic procedures, for example, ion exchange chromatography on Amberlite CG50I, gel filtration on Sephacryl S 200 or hydrophobic chromatography on Phenyl-Sepharose CL-4B, the enzyme may be further purified to a specific activity of 110 U/mg. The substrate spectrum is not changed by this. The molecular weight of the D-2-hydroxy-4-methylpentanoic acid dehydrogenase was determined by gel filtration on Sephacryl S 200 superfine to be 73,000±10,000 Dalton according to the method of Andrews (Meth. Biochemical Analysis, Vol. 18, 1–53 (1970)). As calibration substances, dextrane-blue, ferritin, aldolase, bovine serum albumin, ovalbumin, chymotrysinogen A and cytochrome C were employed.

The D-2-hydroxy-4-methylpentanoic acid dehydrogenase of the invention can be used on the one hand for preparation of D-2-hydroxycarboxylic acids, and on the other, with an L-aminoacid dehydrogenase for conversion of D-2-hydroxycarboxylic acids into the corresponding optically active L-amino acids. Moreover, the new enzyme can also serve to determine enzymatically the concentrations in aqueous solutions of the 2-ketocarboxylic acids or D-2-hydroxycarboxylic acids used as substrates. When the substrate concentration is low relative to $K_M$, the reaction velocity is linearly depending on the substrate concentration (first order reaction). The determination is very simple to carry out; the change in the extinction of NADH at 340 nm is followed, and the concentration sought is read from an appropriate calibration curve.

The stereoselectivity of the enzymatic conversion was proved in an enzyme membrane reactor. For the regeneration of the NADH consumed in the reduction of the 2-ketocarboxylic acid, a formate dehydrogenase in a sodium formate buffer was added, and, instead of the native NADH, a NADH covalently bound to polyethylene glycol (average molecular weight 20,000) was employed. (Preparation according to DE-PS 28 41 414). The following keto acids were converted individually in the reactor:

2-keto-4-methylpentanoic acid (sodium salt), 2-keto-4-(methylmercapto)-butyric acid (sodium salt) and phenyl pyruvate (sodium salt). The product stream flowing out of the membrane reactor was analyzed continuously in a polarimeter. The signals obtained were evaluated by means of calibration curves which had been obtained from optically active 2-hydroxy acids. Table 3 shows that, under the conditions chosen, very high conversions were attained, and only the D-isomers of the 2-hydroxycarboxylic acids were observed. The results show furthermore that the enzyme of the invention accepts modified NADH of increased molecular weight.

TABLE 3

Reduction of 2-ketocarboxylic acids

| Substrate | Rotation of Production Solution | Stereo-isomer | Product concentration (% conversion) |
|---|---|---|---|
| 2-keto-4-methylpentanoic acid | −0.047° | D | 7.0 mM (100%) |
| 2-keto-4-(methylmercapto)-butyric acid | −0.071° | D | 6.9 mM (98%) |
| 2-keto-3-phenylpropionic acid | −0.115° | D | 7.0 mM (100%) |

The invention is elucidated in greater detail in the following examples:

EXAMPLE 1

Screening of D-2-hydroxy-4-methylpentanoic acid dehydrogenase producers

A screening of 45 strains of the genus Lactobacillus and Leuconostoc from the German Collection of Microorganisms at Goettingen was carried out. The strains were treated in suitable media in shaking flasks, the cells harvested after 20 to 25 hours, and finally disintegrated by ultrasonic treatment. The insoluble cell fragments were centrifuged off, and the clear supernatant used as crude extract. The enzyme activity was determined in a photometric test; the test mixture (3.00 ml) had the following composition: 0.235 mM NADH, 0.79 mM 2-keto-4-methylpentanoic acid and 0.1M pH 7.0 phosphate buffer. The test volume was incubated 10 minutes at 30° C., and the reaction then started by addition of limiting quantities of the enzyme.

The enzyme activity was measured by decrease of the extinction of NADH at 340 nm. Deduction of a blank value was made from a test proceeding without 2-keto-4-methylpentanoic acid. The enzyme activity is given in international units (U), wherein 1 U signifies the consumption of 1 μMol NADH per minute and ml.

The test described does not permit any decision of what sterospecificity the NADH-dependent D-2-hydroxy-4-methylpentanoic acid dehydrogease possesses. The search program was made in this way, since there was interest in both the D-specific and the L-specific dehydrogenase.

A differentiation between the two activities was possible by following the conversion of D-2-hydroxy-4-methylpentanoic acid with NAD+, which is catalyzed only by a D-2-hydroxy-4-methylpentanoic acid dehydrogenase, while the L-2-hydroxy-4-methylpentanoic acid dehydrogenase is inactive with this substrate.

To that end, the following test was used: 3.0 mM NAD+, 6.3 mM D-2-hydroxy-4-methylpentanoic acid and 0.1M phosphate pH 8.0 buffer. The test volume (3.00 ml) was incubated for 10 minutes at 30° C., and the reaction then started by addition of limited quantities of the enzyme. The blank value was deducted obtained from a test without the D-2-hydroxy-4-methylpentanoic acid. In the previous Table 1 the six strains are shown which contain the D-2-hydroxy-4-methylpentanoic acid dehydrogenase of the invention; in addition, the reaction velocities are reported for the enzymatically catalyzed conversions with additional 2-ketocarboxylic acids. The enzyme activity was measured in the test described above, in which the 2-keto-4-methylpentanoic acid was substituted by several other 2-ketocarboxylic acids, as given in Table 1. Lactobacillus casei ssp. pseudoplantarum (DSM 20008) showed the broadest substrate spectrum.

EXAMPLE 2

Dependence of the reaction velocity of the enzymatically catalyzed conversion on pH The reaction velocity of the reduction of 2-keto-4-methylpentanoic acid to D-2-hydroxy-4-methylpentanoic acid in the presence of D-2-hydroxy-4-methylpentanoic acid dehydrogenase was investigated as a function of the pH of the reaction solution. The test mixture (3.00 ml) had the following composition: 0.1 mM NADH, 0.7 mM 2-keto-4-methylpentanoic acid, limiting quantities of enzyme, 0.1M buffer of varying composition and different pH values, as shown in FIG. 1. In FIG. 1, the reaction velocity (expressed as enzyme activity in U/ml) is graphed as a function of pH. The enzyme shows a relatively broad pH optimum between 5.5 and 7, for the reduction reaction.

The reaction velocity of the dehydrogenation of 2-hydroxy-4-methylpentanoic acid to 2-keto-4-methylpentanoic acid, catalyzed by D-2-hydroxy-4-methylpentanoic acid dehydrogenase, was likewise studied as a function of pH. The test mixture had the following composition: 4.5 mM NAD+, 12 mM D,L-2-hydroxy-4-methylpentanoic acid, limiting quantities of enzyme, 0.1M buffer of different compositions, as shown in FIG. 2. The reaction velocity (expressed as enzyme activity in U/ml) of the dehydrogenation reaction shows an optimum in the range of pH 8 to pH 9.

EXAMPLE 3

Storage stability of D-2-hydroxy-4-methylpentanoic acid dehydrogenase as a function of pH D-2-hydroxy-4-methylpentanoic acid dehydrogenase was incubated for 7 days at 4° C. in 0.1M buffer of various compositions at a protein concentration of 0.03 mg/ml. Then the residual activity, as described in Example 2, was determined. In this way, extraordinary pH stability was shown from pH 3.5 to 10.0. After 24 days, 95% of the activity was still demonstrable.

EXAMPLE 4

Dependence of the reaction velocity on the substrate concentrations

The dependence of the reaction velocity in the reduction of 2-keto-4-methylpentanoic acid to D-2-hydroxy-4-methylpentanoic acid on the concentration of the coenzyme NADH was studied in the following test mixture: 0.1M phosphate pH 7.0 buffer, 0.7 buffer, 0.7 mM 2-keto-4-methylpentanoic acid, limiting amounts of enzyme (enriched preparation, after DEAE-cellulose chromatography, see Table 2); the NADH concentration in the test mixture was varied in the range 0.003 to 0.33 mM. It was shown that the optimal reaction velocity was reached at 0.10 mM. The $K_M$-value for for NADH is 0.010 mM. NADPH cannot replace the coenzyme NADH; this was checked up to a test concentration of 0.2 mM.

The reaction speed for reduction of different 2-ketocarboxylic acids was also investigated as a function of the keto acid concentration. For this, the following test mixture was used: 0.1M phosphate buffer for pH 7.0, 0.1 mM NADH and limiting quantities of emzyme (enriched preparation after DEAE-cellulose chromatography, see Table 2). The ketocarboxylic acid concentration was in each case varied from 0.01 to a maximum of 60 mM. The initial reaction velocity, change of extinction at 340 nm/min, was evaluated by non-linear regression of the Michaelis-Menten equation. The kinetic constants $K_M$ and $V_{max}$ are summarized in Table 4.

TABLE 4

Substrate specificity of D-2-hydroxy-4-methylpentanoic acid dehydrogenase from Lactobacillus casei ssp. pseudoplantarum

| Substrate | Max. initial reaction velocity $V_{max}$ ($\mu$Mol $\times$ min$^{-1}$ $\times$ mg$^{-1}$) | $K_M$ Value (M) |
|---|---|---|
| 2-ketobutyric acid | 45.9 | $1.7 \times 10^{-3}$ |
| 2-ketopentanoic acid | 59.1 | $1.1 \times 10^{-4}$ |
| 2-ketohexanoic acid | 58.4 | $1.1 \times 10^{-4}$ |
| 2-ketooctanoic acid | 54.0 | $3.1 \times 10^{-4}$ |
| 2-keto-3-methyl-butyric acid | 16.9 | $4.8 \times 10^{-3}$ |
| 2-keto-3-methyl-pentanoic acid | 26.2 | $2.2 \times 10^{-3}$ |
| 2-keto-4-methyl-pentanoic acid | 27.4 | $6.0 \times 10^{-5}$ |
| 2-keto-4-(methylmercapto)-butyric acid | 82.1 | $6.2 \times 10^{-4}$ |
| 2-keto-3-mercaptopropionic acid | 104.5 | $4.0 \times 10^{-4}$ |
| 2-keto-3-phenylpropionic acid | 304.4 | $1.5 \times 10^{-4}$ |

The dependence of the reaction velocity on the NAD+ concentration in the dehydrogenation of D-2-hydroxy-4-methylpentanoic acid was studied in the following test mixture: 0.1M phosphate buffer at pH 8.0, 12 mM D,L-2-hydroxy-4-methylpentanoic acid, limiting quantities of enzyme. The NAD+ concentration was varied in the range from 0.10 to 10 mM, and the increase in extinction from NADH generated in the reaction measured at 340 nm. It was shown that the optimum conversion is reached at a concentration of 4.5 mM. The $K_M$ value for NAD+ is 0.45 mM. NADP cannot replace the coenzyme NAD+; this was checked at test concentrations up to 10 mM.

The dependence of the reaction speed on the concentration of different 2-hydroxycarboxylic acids for the dehydrogenation of D-2-hydroxycarboxylic acids was tested in the following test mixture: 0.1M phosphate buffer at pH 8.0, 4.5 mM NAD+ and limiting quantities of enzyme. The concentration of D-2-hydroxycarboxylic acid was varied in the range from 0.1 to a maximum of 30 mM. Inasmuch as no chiral D-2-hydroxycarboxylic acid was available, the racemate was added. The NADH generated in the reaction was determined at 340 nm. The initial reaction velocity was evaluated according to Michaelis-Menten, and the kinetic constants $V_{max}$ and $K_M$ determined by non-linear regression. The kinetic constants found are summarized in Table 5.

TABLE 5

Substrate specificity of D-2-hydroxy-4-methylpentanoic acid dehydrogenase fron Lactobacillus casei ssp pseudoplantarum

| Substrate | Max. initial reaction velocity $V_{max}$ ($\mu$Mol $\times$ min$^{-1}$ $\times$ mg$^{-1}$) | $K_M$ Value (M)* |
|---|---|---|
| D,L-2 hydroxypentanoic acid | 10.8 | $7.0 \times 10^{-4}$ |
| D,L-2-hydroxyhexanoic acid | 11.3 | $4.7 \times 10^{-4}$ |

TABLE 5-continued

Substrate specificity of D-2-hydroxy-4-methylpentanoic acid dehydrogenase fron Lactobacillus casei ssp pseudoplantarum

| Substrate | Max. initial reaction velocity $V_{max}$ ($\mu$Mol $\times$ min$^{-1}$ $\times$ mg$^{-1}$) | $K_M$ Value (M)* |
|---|---|---|
| D,L-2-hydroxyoctanoic acid | 10.0 | $3.1 \times 10^{-4}$ |
| D,L-2-hydroxy-4-methyl-pentanoic acid | 20.2 | $1.4 \times 10^{-3}$ |
| D-2-hydroxy-4-methyl-pentanoic acid | 20.2 | $1.4 \times 10^{-3}$ |
| D,L-2-hydroxy-4-(methylmercapto)-butyric acid | 2.6 | $1.5 \times 10^{-3}$ |
| D,L-2 hydroxy-3-phenyl-propionic acid | 32.6 | $1.1 \times 10^{-3}$ |

*calculation is based on the assumption that the D-2-hydroxy carboxylic acid content of the racemic mixtures was 50%

EXAMPLE 5

Stereospecificity of the reduction of 2-keto-4-methylpentanoic acid and other 2-ketocarboxylic acids with the dehydrogenase of the invention from Lactobacillus casei ssp. pseudoplantarum (DSM 20008)

Continuous synthesis of D-2-hydroxycarboxylic acids from the corresponding 2-ketocarboxylic acids is possible in an enzyme membrane reactor with the use of high-molecular weight NADH bound to polyethylene glycol. The PEG-NADH is prepared according to DE-PS No. 28 41 414. The modified coenzyme and the added enzyme, formate-dehydrogenase (Preparation according to Kroner et al. (1982), J. Chem. Tech. Biotechnol. 32, 130–137) and the D-2-hydroxy-4-methylpentanoic acid dehydrogenase are retained via an ultrafiltration membrane YM 5 (Product of the Amicon Company, Witten) in the reactor, while the lower-molecular weight constituents of the reaction solution, the optically active 2-hydroxycarboxylic acids formed, any unconverted substrate (optically inactive keto acids!) and the buffer employed are removed continuously from the reactor. The reactor volume is kept constant, by adding keto acid and sodium formate buffer from a reservoir at the same rate as the ultrafiltrate leaves the reactor. The reactor volume was 10 ml, the concentration of PEG-NADH 0.20 mM, and 9 U D-2-hydroxy-4-methylpentanoic acid dehydrogenase (27 U/mg) and 30 U formate-dehydrogenase were fed into the reactor. The substrate solution contained 300 mM sodium formate buffer of pH 7.0 and 7.0 mM of the corresponding 2-ketocarboxylic acid. The reaction solution was pumped over the membrane continuously with a peristaltic pump at 30 ml/hour. About 3 ml ultrafiltrate per hour was obtained. The ultrafiltrate was led continuously through a polarimeter cell (Perkin Elmer Type 241). The determinations were carried out at 463 nm and 25° C. From the measured rotatory value, the product concentration was determined from a calibration curve. The calibration curves were prepared with optically active 2-hydroxycarboxylic acids in 300 mM sodium formate buffer of pH 7.0. For this, the following preparations were used: L-phenyllactic acid (Sigma Company, Munich), L-2-hydroxy-4-methylpentanoic acid (Sigma Company, Munich), and D-2-hydroxy-4-(methylmercapto)-butyric acid (Degussa Company, Hanau). The conversion in the membrane reactor was followed over a period of 15 hours. The stationary values obtained are shown in Table 3.

In the same way, the stereoselectivity with the substrate 2-keto-4-methylpentanoic acid of the D-2-hydroxy-4-methylpentanoic acid dehydrogenases produced from the other microorganisms of Table 1 was checked. For this, the crude extract of Example 1 was added as enzyme source. The formation only of D-2-hydroxy-4-methylpentanoic acid was observed, at conversions between 96 and 100%.

What is claimed is:

1. The enzyme D-2-hydroxy-4-methylpentanoic acid-dehydrogenase.
2. The microbiologically produced enzyme of claim 1.
3. The enzyme of claim 1 characterizied by the following properties:
    (a) catalyzes, with the coenzyme nicotinamide-adeninedinucleotide (NAD+), the dehydrogenation of D-2-hydroxy-4-methylpentanoic acid to 2-keto-4-methylpentanoic acid,
    (b) catalyzes, with the coenzyme NAD+, the dehydrogenation of additional D-2-hydroxycarboxylic acids to the corresponding 2-ketocarboxylic acids and especially shows activity with respect to D-2-hydroxypentanoic acid, D-2-hydroxyhexanoic acid, D-2-hydroxyoctanoic acid, D-2-hydroxy-4-(methylmercapto)-butyric acid and D-2-hydroxy-3-phenylpropionic acid,
    (c) catalyzes the stereoselective reduction of 2-keto-4-methylpentanoic acid to D-2-hydroxy-4-methylpentanoic acid with NADH as coenzyme,
    (d) catalyzes the stereoselective reduction of additional 2-ketocarboxylic acids, especially of 2-ketobutyric acid, 2-ketopentanoic acid, 2-keto-3-methylbutyric acid, 2-ketohexanoic acid, 2-keto-3-methylpentanoic acid, 2-ketooctanoic acid, 2-keto-3-mercaptopropionic acid, 2-keto-4-(methylmercapto)-butyric acid and 2-keto-3-phenylpropionic acid to the corresponding D-2-hydroxycarboxylic acids, with NADH as coenzyme,
    (e) an optimal pH-range of 7.5 to 9.0 for the dehydrogenation reaction,
    (f) an optimal pH-range of 5.5 to 7.0 for the reduction reaction, and
    (g) a pH-stability range of 3.5 to 10.
4. The enzyme of claim 1 produced by culturing a Lactobacillus microorganism or a Leuconostoc microorganism.
5. The enzyme of claim 4 wherein said microorganism is *Lactobacillus casei ssp. pseudoplantarum*.
6. The enzyme of claim 4 wherein said microorganism is *Lactobacillus casei ssp. rhamnosus*.
7. The enzyme of claim 4 wherein said microorganism is *Lactobacillus casei, ssp alachosus*.
8. The enzyme of claim 4 wherein said microorganism is *Leuconostoc oenos*.
9. The enzyme of claim 4 wherein said microorganism is *Leuconostoc lactis*.
10. The enzyme of claim 4 wherein said microorganism is *Leuconostoc mesenteroides*.
11. A method of producing the enzyme D-2-hydroxy-4-methylpentanoic acid dehydrogenase, which comprises culturing a microorganism of the genus Lactobacillus or Leuconostoc and recovering the resulting produced D-2-hydroxy-4-methylpentanoic acid dehydrogenase from the cultured microorganism.
12. A method in accordance with claim 11 wherein said microorganism is selected from the group consisting of *Lactobacillus casei spp. pseudoplantarum, Lactobacillus casei ssp. rhamnosus, Lactobacillus casei ssp. alachosus, Leuconostoc oenos, Leuconostoc lactis* and *Leuconostoc mesenteroides*.
13. A method of enzymatically converting D-2-hydroxy-4-methylpentanoic acid, D-2-hydroxypentanoic acid, D-2-hydroxyhexanoic acid, D-2-hydroxyoctanoic acid, D-2-hydroxy-4-(methylmercapto)-butyric acid, D-2-hydroxy-3-phenylpropionic acid to the corresponding ketocarboxylic acid and of enzymatically converting 2-keto-4-methylpentanoic acid, 2-ketobutyric acid, 2-ketopentanoic acid, 2-keto-3-methylbutyric acid, 2-ketohexanoic acid, 2-keto-3-methylpentanoic acid, 2-ketooctanoic acid, 2-keto-3-mercaptopropionic acid, 2-keto-4-(methylmercapto)-butyric acid and 2-keto-phenylpropionic acid to the corresponding D-2-hydroxycarboxylic acid, which comprises employing the enzyme D-2-hydroxy-4-methylpentanoic acid-dehydrogenase.
14. A method in accordance with claim 13 wherein said enzyme D-2-hydroxy-4-methylpentanoic acid-dehydrogenase is derived from a Lactobacillus or a Leuconostoc microorganism.
15. A method in accordance with claim 14 wherein said microorganism is selected from the group consisting of *Lactobacillus casei ssp. pseudoplantarum, Lactobacillus casei ssp. rhamnosus, Lactobacillus casei, ssp. alachosus, Leuconostoc oenos, Leuconostoc lactis* and *Leuconostoc mesenteroides*.

* * * * *